(12) United States Patent
Trevino et al.

(10) Patent No.: US 12,370,082 B2
(45) Date of Patent: Jul. 29, 2025

(54) IMPLANT DELIVERY DEVICE

(71) Applicant: ALCON INC., Fribourg (CH)

(72) Inventors: Leo Anthony Trevino, Hurdle Mills, NC (US); Cheng Li, Durham, NC (US); Tyler Pegoraro, Raleigh, NC (US); Stuart Williams, Raleigh, NC (US); Thomas Shepard, Rolesville, NC (US); Peter Andrew Smith, Cary, NC (US); Matthew Charles Walker, Lillington, NC (US); Andrew John Corson, Apex, NC (US); Thomas Ralph Blackburn, III, Holly Springs, NC (US); Stephen James Couse, Apex, NC (US)

(73) Assignee: ALCON INC., Fribourg (CH)

( * ) Notice: Subject to any disclaimer, the term of this patent is extended or adjusted under 35 U.S.C. 154(b) by 651 days.

(21) Appl. No.: 17/714,333

(22) Filed: Apr. 6, 2022

(65) Prior Publication Data
US 2022/0331156 A1 Oct. 20, 2022

Related U.S. Application Data

(60) Provisional application No. 63/176,056, filed on Apr. 16, 2021.

(51) Int. Cl.
*A61F 9/00* (2006.01)
(52) U.S. Cl.
CPC .................... *A61F 9/0017* (2013.01)
(58) Field of Classification Search
CPC ............ A61F 9/0017; A61F 2250/0007; A61F 2250/0069; A61J 1/201; A61J 1/2055; A61M 2005/31508; A61M 2037/0023; A61M 2037/0061; A61M 2210/0612; A61M 37/0015; A61M 5/2033; A61M 5/31; A61M 5/3293; A61M 5/2053; A61M 5/34; A61M 5/344; A61M 5/346; A61M 5/347;
(Continued)

(56) References Cited

U.S. PATENT DOCUMENTS

2013/0158561 A1\* 6/2013 Bhagat ................. A61F 9/0017
606/107
2015/0038905 A1\* 2/2015 Andino ............... A61M 5/2053
604/117
(Continued)

FOREIGN PATENT DOCUMENTS

WO 2014/179698 A2 11/2014
WO 2017/158365 A2 9/2017

*Primary Examiner* — Scott J Medway
*Assistant Examiner* — Anh T Bui
(74) *Attorney, Agent, or Firm* — MCDONNELL BOEHNEN HULBERT & BERGHOFF LLP (57) ABSTRACT

Implant delivery devices, methods of device assembly and methods of using those devices are presented where the delivery device uses an automatic implant delivery mechanism that eliminates variability in pusher wire speeds by providing a needle assembly having one or more implants positioned within a proximal end of a needle cannula, a dampener assembly and a shuttle assembly located within a housing along with the activation member which holds the shuttle assembly in cocked or pre-tensioned state. A lock can be engaged with the activation member to prevent premature firing or triggering of the device.

20 Claims, 7 Drawing Sheets

(58) Field of Classification Search
CPC ........ A61M 5/348; A61M 5/349; A61M 5/46; A61M 5/482; A61M 5/484
See application file for complete search history.

(56) References Cited

U.S. PATENT DOCUMENTS

| | | | |
|---|---|---|---|
| 2021/0169689 A1* | 6/2021 | Bley .................... | A61F 9/0017 |
| 2023/0103975 A1* | 4/2023 | Howard-Sparks .... | A61F 9/0017 604/506 |

* cited by examiner

IMPLANT DELIVERY DEVICE

CROSS REFERENCE TO RELATED APPLICATIONS

The present application is claims priority to U.S. Provisional Application No. 63/176,056 filed Apr. 16, 2021, which is herewith incorporated by reference into the present application.

TECHNICAL FIELD

This disclosure is directed to implant delivery devices, for example devices designed for delivering drugs as well as pharmaceutical compositions comprising a drug to an eye of a patient.

BACKGROUND

The use of intraocular injections is gaining prevalence worldwide and has become a common treatment for retinal diseases or disorders, such as macular degeneration, retinal vein occlusion and diabetic retinopathy, to name only a few. Patients with these conditions risk permanent loss of central vision. Treatment as early and thoroughly as possible is important to save vision and prevent any further loss with these conditions. Intraocular injections maximize treatment effectiveness with a highly targeted drug therapy that is accurately delivered as an implant to parts of the eye for which administration is not possible via topical administration, such administration to the vitreous humor near the retina in the back of the eye. Although delivery devices for insertion of an implant into eye tissue are known, such devices require that a user, for example an ophthalmologist, manually operate the device during the actual implant insertion process. Unfortunately, this manual manipulation of the insertion procedure can lead to an inconsistent implant delivery speed which can result in an inadvertent impacting of non-target tissues within the eye (i.e., hitting the retina during an intravitreal injection).

A need therefore exists to provide an implant delivery device and method of use that will consistently deliver drug eluting, biocompatible micron sized implants through a cannula to a desired target location in the eye. The implant delivery device should be designed so that the implant delivery speed is independent of the force with which the trigger button is pressed by the user.

SUMMARY

Provided herein are heretofore unknown auto delivery devices that eliminate variability in pusher wire speeds by decoupling the implant speed of delivery from user input.

The present disclosure provides implant delivery devices, methods of device assembly and methods of using those devices, all of which results in an increase in safety to the subject by limiting the implant delivery speed at which the implant is inserted into the target tissue insertion site. The automatic, non-user controlled, delivery speeds of devices of the present disclosure reduce the potential for undesirable impact of the implant with non-targeted tissues of the eye. User independent implant delivery speed also ensures that the implants have sufficient speed to fully exit the lumen of the needle cannula prior to the needle being withdrawn from the eye. Visual indication that shows when the implants have been delivered from the delivery device also contributes to consistent and safe implant delivery process.

The embodiments described in this disclosure relate generally to medical implant delivery apparatuses and methods. In the present disclosure, when the term "proximal direction" is used, this refers to the direction pointing away from the dose delivery site during use of the medicament delivery device. When the term "proximal part/end" is used, this refers to the part/end of the delivery device, or the parts/ends of the members thereof, which under use of the medicament delivery device is/are located furthest away from the dose delivery site. Correspondingly, when the term "distal direction" is used, this refers to the direction pointing towards the dose delivery site during use of the medicament delivery device. When the term "distal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component. Similarly, the terms "transverse", "transversal" and "transversally" refer to a direction generally perpendicular to the longitudinal direction.

A number of embodiments of the present disclosure are presented herein including implant delivery devices for automatically inserting one or more implants into tissue without requiring input from the device user to manually push the implant into the desired tissue location. Likewise, the present disclosure provides methods of fabricating and/or assembling the implant delivery devices and methods of using and/or operating the implant delivery devices. The delivery device can be configured and manufactured for a single use. In other words, the delivery device cannot be reused to perform an implantation of an implant. Such a configured device is considered a disposable device in that the device is deposited into a Sharps container or similar receptacle upon completion of the implant procedure. The user of the devices disclosed herein is typically a health care professional, for example an ophthalmologist. The delivery device has an elongated, generally spherical or oval housing that is attached to a needle assembly and contains a pusher wire fixed to a shuttle assembly that interacts with a dampener assembly. A removable lock and an activation member can also be part of the delivery device.

One possible method of assembly includes providing each of the structural components of the needle assembly and arranging and connecting those components to form the needle assembly. Completion of the needle assembly includes placing and inserting one or more implants into the proximal end of the needle cannula. Separately, the dampener assembly and shuttle assembly are fabricated and then placed with a section of the housing along with the activation member which holds the shuttle assembly in cocked or pre-tensioned state. The lock is inserted and engaged with the activation member to prevent premature firing or triggering of the device. The needle assembly is then attached to the housing.

One possible method of using the implant delivery devices of the present disclosure includes removing the lock from the housing and the protective cap from the needle assembly, positioning the needle cannula at the target tissue implant delivery site, manually pushing the delivery device in distal direction to insert the distal end of the needle cannula into a biological membrane, the vitreous humor or tissue, pushing the activation member relative to the housing of the delivery device to initiate the automatic implant insertion procedure which results when the shuttle assembly is released from the activation member. Axial biasing forces from the pretensioned shuttle assembly combined with the dampener assembly causes automatic axial movement of a pusher wire within the needle cannula relative to the housing. Axial movement of the pusher wire pushes the implant through the needle cannula and out the distal end into the tissue. Monitoring a change in the delivery window located in the housing notifies the user when the placement of the implant into the tissue is complete and signaling the time to remove the needle cannula from the tissue.

BRIEF DESCRIPTION OF THE FIGURES

The specific embodiments of the inventive concept will now be described, by way of example, with reference to the accompanying drawings, in which.

DETAILED DESCRIPTION

Figure 1:
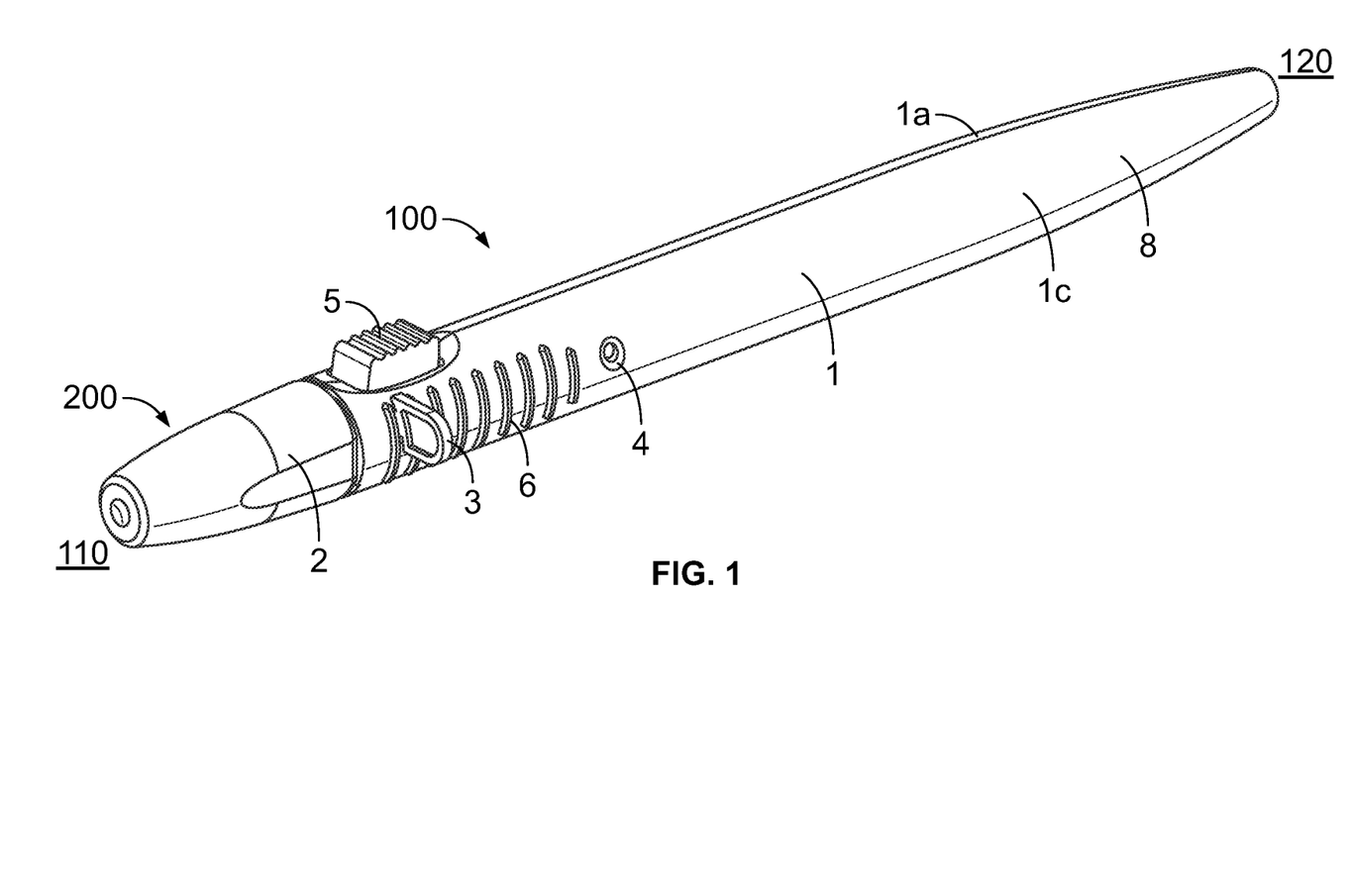
FIG. 1 is a perspective view of one possible design of the implant delivery device of the present disclosure.

Specific embodiments of the implant delivery device of the present disclosure will now be disclosed with reference to FIGS. 1-8. As shown in FIG. 1, the delivery device 100 has an elongated substantially cylindrical body or outer housing 1 defining a longitudinal flow path or axis 105, the delivery device has a distal end 110 and a proximal end 120. The housing 1 can be formed from sections, for example two halves 1a and 1c, that are permanently connected to each other during assembly of the device. As used in this disclosure, the term "permanent" or "permanently" is meant to describe a connection or attachment that is not releasable or reusable and where the parts connected cannot be separated from each other without forcing, breaking or destroying one or more of the parts or connectors holding the parts together. For example, a screw thread connector is typically reusable such that one part can be unscrewed from another part. However, in contrast a glued or welded connection between parts does not allow separation of the parts from each other without causing damage. In some cases, a particular type of connector can be designed as either releasable or permanent. For example, a snap fit connection can be either a permanent connector or provide a releasable connection between parts.

When assembled, the housing 1 can have a generally tapered proximal end 8 that provides an ergonomic benefit when holding and using the device to deliver the implant into tissue. The tapered proximal end can also provide a convenient prompt to the user of where on the housing to grasp/hold the delivery device. To further indicate where the user should grasp or hold the delivery device during use, the outer surface of the distal end of housing 1 can have a grip surface 6. This grip surface can be comprised of a plurality of surfaces in the form of raised or proud surfaces or ribs, knurled or roughened surfaces, inlays or overlays of a tactile/soft touch material, stippling features, dimples, or any other features that indicates to the user where to grab or hold the device during use. Another feature of grip surface 6 is that it can provide a pushing or bearing surface that the user can use to deploy the device axially in the distal direction during insertion of the needle at the desired implant insertion location site. Another device feature that can assist a user in moving or pushing the needle into the target tissue location is the raised surface of the activation member 5. In some cases, it is desirable to include a pushing surface 9 that provides the user a tactile feel and/or leverage feature during operation of the implant delivery device 100.

The housing may also contain a view port 4, for example a cut-out or window, that allows a user of the delivery device to monitor the operation of the device and to visibly notify or otherwise indicate when the implant insertion is completed. One possible method of providing visual notification is to use a shutter effect or mechanism, for example before the implant is fully delivered, a shutter or blocking structure appears in or fills the window 4 and upon completion of the implant delivery the shutter or blocking structure moves to open the window, so that nothing appears. This shutter could be a portion or section one of the internal components of the delivery device, for example the shuttle 18 or shaft 30 (see FIG. 3). The shuttle can have a distinctive color or other design to aid in the visibility.

Figure 2:
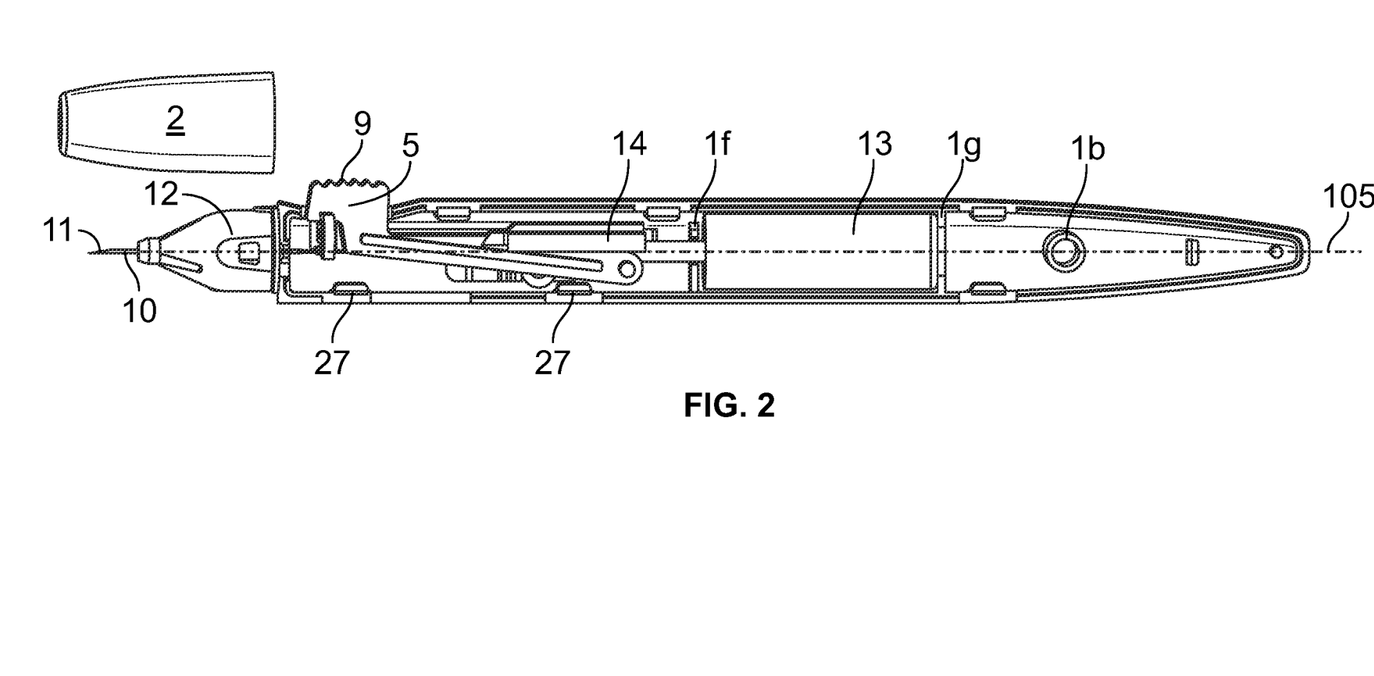
FIG. 2 illustrates the delivery device of FIG. 1 where the protective cap is removed and one-half section of the housing is removed to show the shuttle assembly, activation member, lock and dampener assembly.

The housing 1 can also have a cut-out 1i (see FIG. 3) located at the distal end portion that will slidably accept lock 3 having an anvil stop surface 3a and a retaining detent 3b that can be configured to engage a portion of the housing 1 to prevent premature or unintended disengagement from a locked position. Lock 3 is configured to have two positions, a locked position and an unlocked position. FIGS. 1 and 2 show the lock 3 in the first or locked position where the anvil stop surface abuts and prevents movement of the activation member 5, which in turn prevents activation of the implant delivery device. The second or unlocked position is where the user has removed and physically separated lock 3 from the housing 1, for example by pulling the lock transversely relative to the longitudinal axis 105 to overcome the reversible retaining detent 3b. Once lock 3 is removed from the delivery device 100, the activation member 5 is no longer blocked from moving relative to both the housing and the shuttle assembly 14, more specifically shuttle 18, as will be explained in more detail below. When in the first or locked position, lock 3 can function as anti-rolling feature. i.e., the protruding structure of the lock will prevent the delivery device from uncontrollably rolling on a flat surface, such as, inadvertently rolling off a tabletop. A gripping tab 3c can be provided that extends radially from the lock past the outside surface of the housing and is shaped so that a user can grasp lock 3 to remove it from housing 1.

Figure 6:
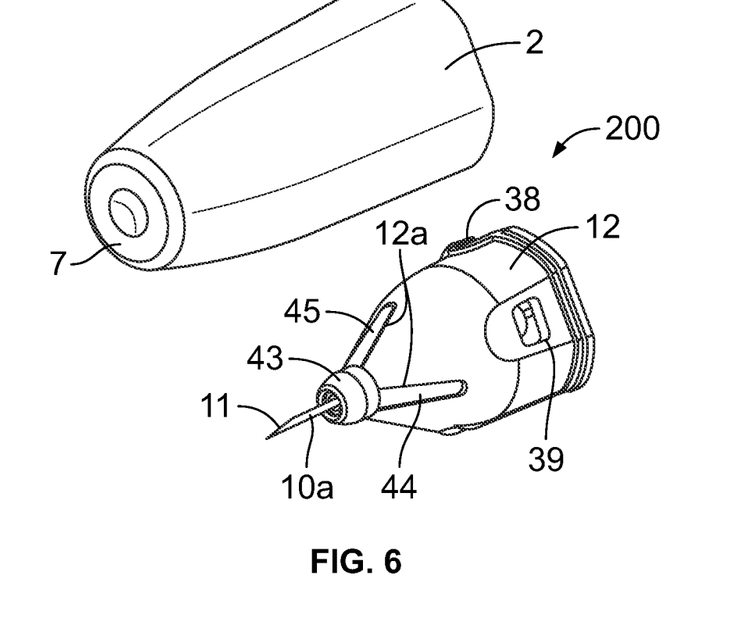
FIG. 6 is a perspective view of the needle assembly of the delivery device of FIG. 1.
Figure 7:
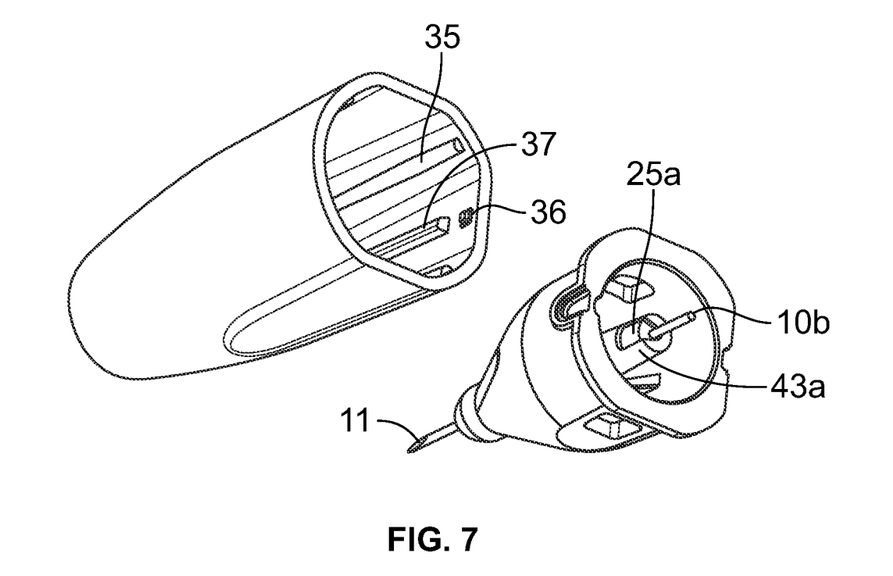
FIG. 7 is another perspective view of the needle assembly of the delivery device of FIG. 1.

Housing 1 also can have hub connector 26 (see FIG. 3) that is configured to engage with a needle assembly 200 (see FIG. 6). The needle assembly can comprise protective cap 2, an outer needle hub 12, an inner needle hub 43 and needle cannula 10 (see FIG. 3). Needle cannula 10 has a distal end 10a and an open proximal end 10b (see FIG. 6). Distal end 10a is configured with one or more bevels 11 that terminate at or define a pointed/sharp terminal end of the needle cannula. The open proximal end 10b is configured to accept one or more implants that are configured to be pushed out of the distal end 10a by pusher wire 24 after insertion of the needle cannula 10 into the target implant insertion site followed by activation of delivery device 100. FIGS. 6 and 7 illustrate in detail one possible configuration of the needle assembly 200 that can have a protective cap 2 which is releasably connected to outer needle hub 12 through reversible snap fits comprising elements 36, 37, 38. The protective cap 2 is directly connected to the outer needle hub 12, as opposed to a direct connection to housing 1. This allows for a separate and independent fabrication of the needle assembly 200 where the integrity of the distal end 10a of the needle cannula 10 is maintained and protected prior to the final assembly of the delivery device. The protective nature of the cap 2 is especially beneficial during 1) the implant insertion procedure where one or more implants are inserted into the proximal end 10b of the needle cannula and 2) the subsequent insertion of the distal end of pusher wire 24 into the proximal end 10b during the final assembly of the delivery device.

Protective cap 2 can have a truncated or flat terminal end 7, i.e., the distal end of the cap 2 has a non-oval or non-rounded shaped distal end. When the cap 2 is fabricated using a clear, transparent or translucent material, this truncated end 7 allows the user to more easily observe if one or more implants, or a fragment of an implant, may have inadvertently fallen out of the distal end 10a of needle cannula 10. Needle cannula 10 can be axially and rotationally fixed to the inner hub 43, or optionally cannula holder 25 through a pressed fit or through the use of an adhesive. The cannula holder 25 can have an alignment peg 25a that fits into a corresponding slot 43a in the inner needle hub 43 in order to achieve a predetermined orientation of the bevel 11 relative to orientation projections 44, 45 on the inner needle hub 43. In one possible configuration, the orientation projections are designed to cooperate with slots 12a on the outer needle hub 12 so that the bevel 11 will face upward in a line-of-sight of the user and in general alignment with the pushing surface 9 of the activation member 5.

Hub connector 26 at the distal end of housing 1 can be a permanent, non-reversible connector that engages with a cooperating connector on the needle assembly, for example the cut-out 39 in outer needle hub 12 shown in FIG. 6. In this possible hub connector configuration, there can be two or more hub connectors 26 located on a neck portion 38 of housing 1 at the distal end, where each hub connector 26 could be a flexible finger that irreversibly forms a snap fit with two or more cut-outs 39 on the outer needle hub 12. The inside surface of housing 1 can be configured with a longitudinal pocket 1e (see FIG. 3) that provides a sliding path for shuttle assembly 14, particularly for the outside edges 18b of the shuttle 18 so that the shuttle assembly 14 can smoothly and uninterruptedly slide relative to both the housing 1 and the dampener assembly 13 once the delivery device is activated by the user.

Figure 3:
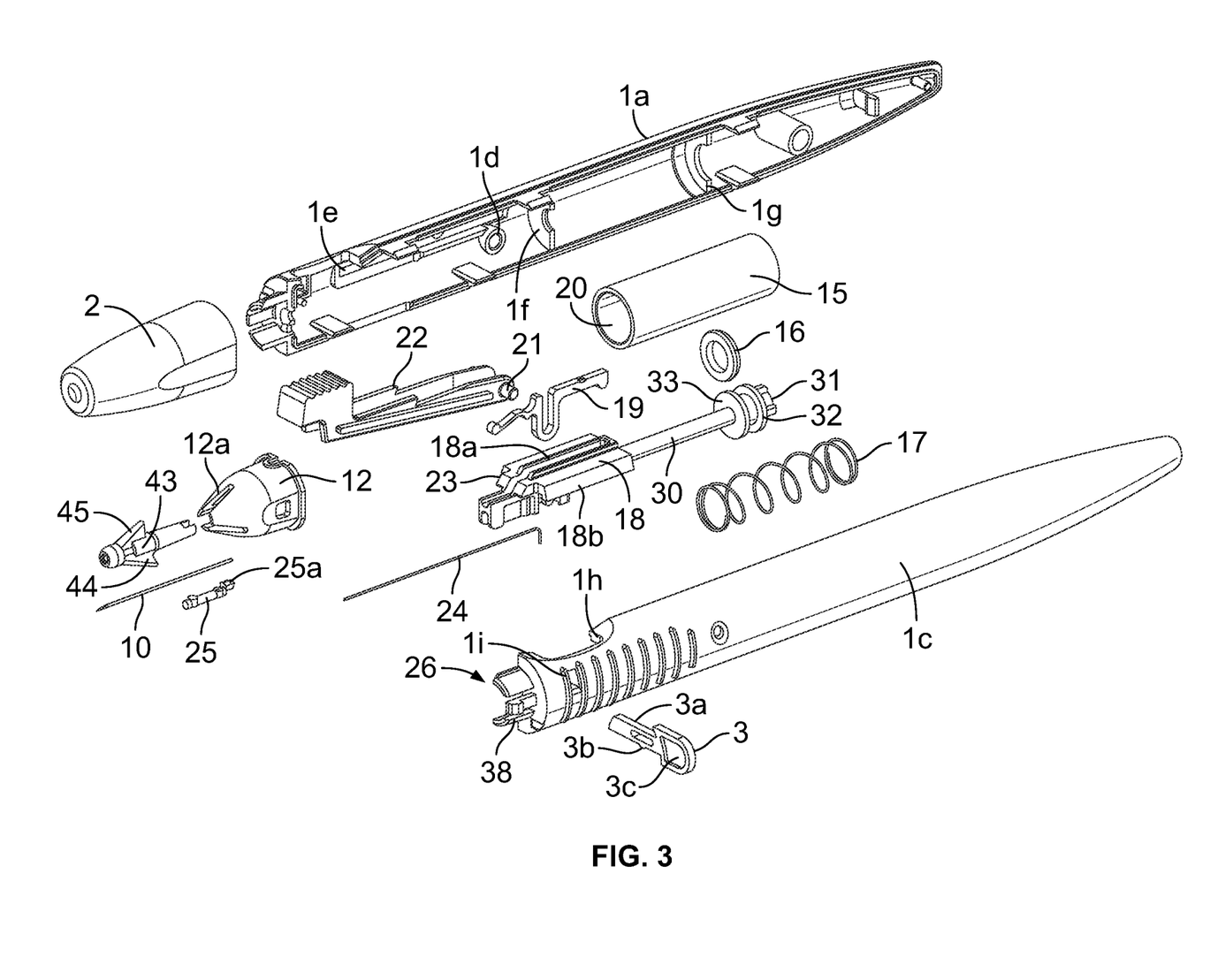
FIG. 3 is a perspective exploded view of the delivery device of FIG. 1.
Figure 5:
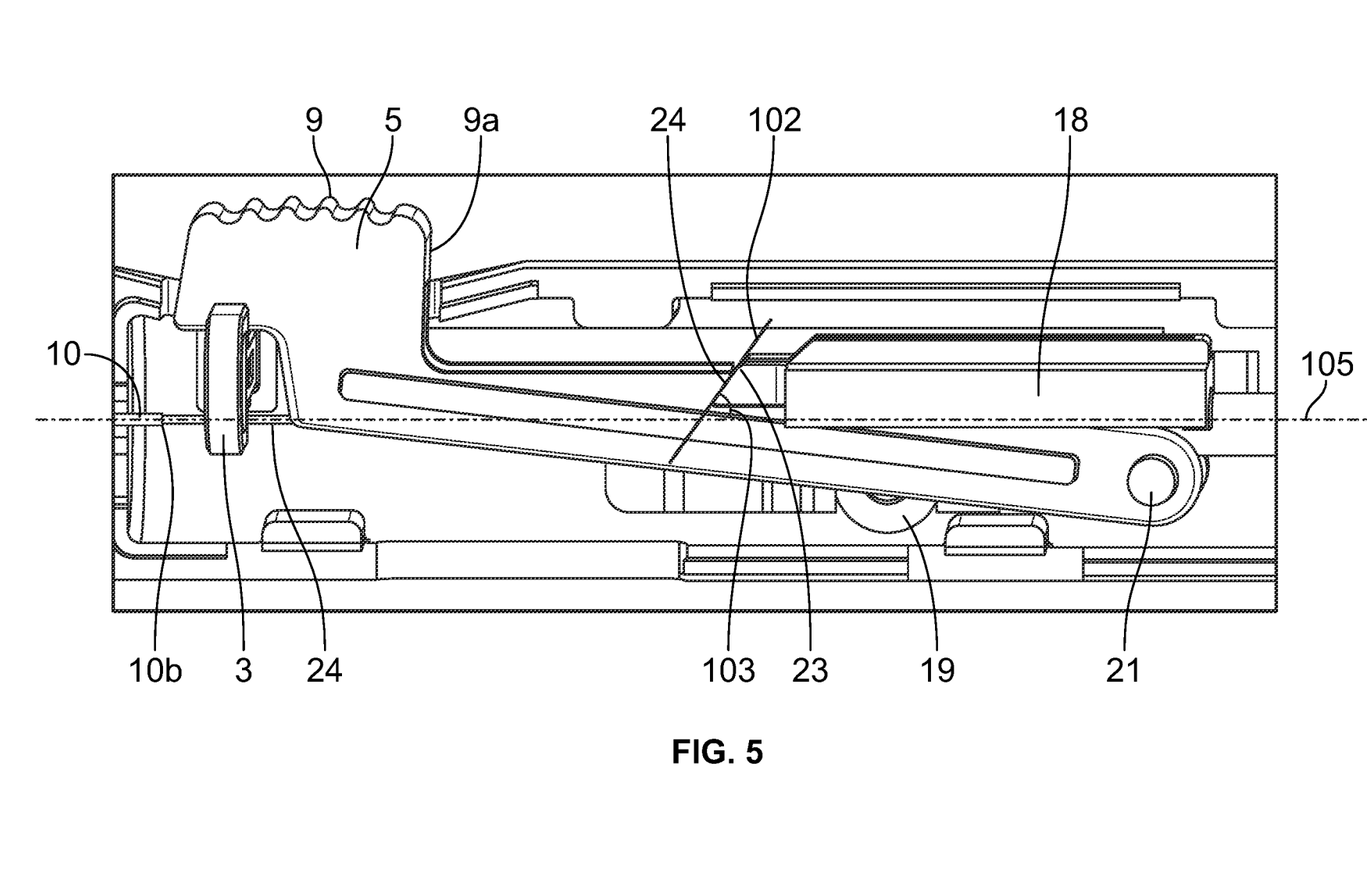
FIG. 5 is a partial cross-sectional view of the delivery device of FIG. 1 illustrating the engagement of the activation member with the shuttle and with the lock.

On the inside of housing 1 there can be a pivot point 1d that allows the distal end of activation member 5 to move radially relative to the housing 1 (see FIGS. 3 and 5). In one possible configuration, the activation member 5 has a pin 21 that is rotatably engaged, but axially fixed, with a cup-shaped pivot point 1d. Activation member 5 can take the form of a push button having push surface 9 where the push surface extends outward through cut-out 1h in housing 1 (see FIG. 3) FIG. 5 illustrates a possible design of activation member 5 and its relationship to shuttle 18 and lock 3 when the device is in the locked (pre-activated) configuration. The push surface 9 can be configured to extend beyond the outer surface of the housing a fixed distance to define a proximal facing surface 9a that the user can press against to assist in moving the delivery device, and needle cannula, axially during insertion of the needle into the tissue at the implant insertion site. Likewise, grip surface 6 (see FIG. 1) can also be used to provide leverage during needle insertion. Each of the housing halves 1a and 1c can have a pivot point 1d such that when the push surface 9 of activation member 5 is pushed downward and slightly radially in a transverse direction relative to axis 105, the pin 21 located at the proximal end of activation member 5 will swing or pivot about pivot point 1d (see FIG. 3).

Each half of the housing can also have connectors 1b and 27 that are configured to align with and secure one housing half to the other half. Two bearing walls 1f and 1g positioned on the inside surface of the housing that can provide fixed axial supports for the dampener assembly 13, which comprises dampener housing 15 and resilient member 17 (see FIG. 3). The dampener housing 15 can be positioned between the bearing walls 1f and 1g during device assembly to prevent axial movement of the dampener housing 15 relative to the housing 1. The dampener housing can have an inside surface 20 and a proximal end wall 39 (see FIG. 4) having a distal facing surface that supports the proximal end of resilient member 17.

Figure 4:
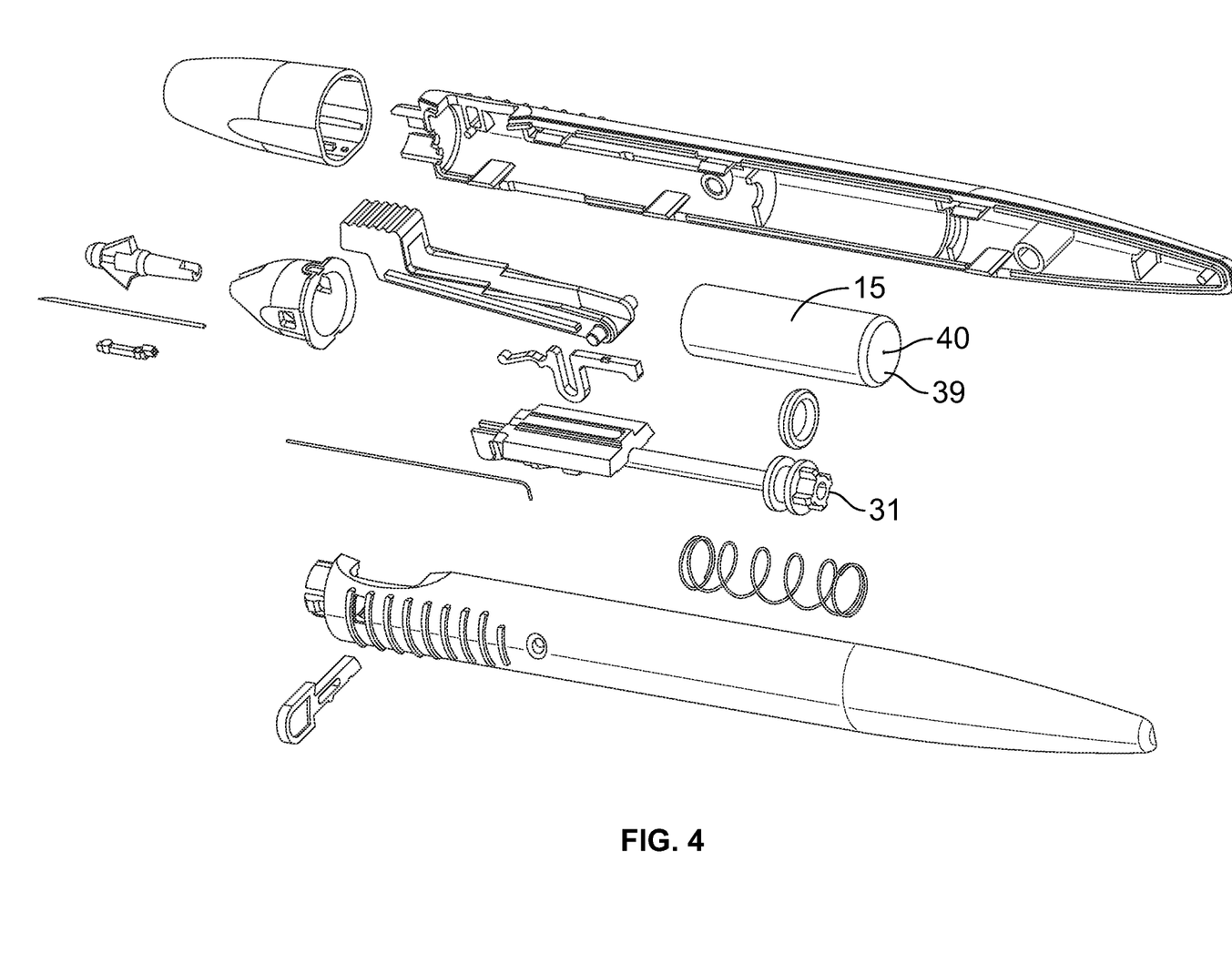
FIG. 4 is another perspective exploded view of the delivery device of FIG. 1.

The resilient member 17 is compressed, or otherwise in a pre-biased state when the delivery device is in the pre-activated state such that it exerts a distally directed force on the shuttle assembly 14. The resilient member 17 can take the form of a compression spring, a torsion spring, a clock spring, or one or more biased levers. The inside surface 20 of the dampener housing 15 can contain a lubricant (wet or dry) that is selected to provide a desired sliding movement, e.g., speed, of the friction slider 16 that is part of the shuttle assembly 14 (see FIG. 2). The sliding movement of the shuttle assembly relative to the housing 1 and dampener assembly 13 can be further controlled by incorporation of an orifice or vent 40 in the dampener housing 15. FIG. 4 illustrate a possible location of vent 40 which is configured as a through hole in the proximal end wall 39. As the friction slider 16 can form an airtight seal with the inside surface 20 of the dampener housing 15, axial movement of the shuttle assembly 14 will tend to create a vacuum on the proximal side of the friction slider 16 which would retard or stop the axial movement of the shuttle assembly. Providing vent 40 allows for air to enter the dampener housing as the friction slider 16 moves distally. The orifice size of vent 40 is selected to achieve a desired or predetermined sliding speed of the shuttle assembly. In addition to varying the size of the vent 40, the strength of resilient member 17 can also be selected to achieve a desired automatic sliding speed, i.e., implant insertion speed. Additionally, the selection of a particular lubricant that is added to the inside surface 20 can also affect the implant insertion speed. An example lubricant that has demonstrated excellent function with particular material combinations is Nyemed 7471 on EPDM O-ring and ABS dampener.

The distal end of resilient member 17 is configured form a bearing engagement with a support 31 located at a proximal end portion of the shuttle assembly 14. This support 31 can be configured to prevent deformation of the resilient member 17 by the inclusion of one or more raised proximally extending projections. FIG. 4 illustrate one possible design of the support 31 where a cylindrical projection having a plurality of radial projections is configured to abut and fit within the distal end of resilient member 17. As mentioned, the resilient member 17 is preloaded when the delivery device is in the pre-activated state. For example, when the resilient member is a compression spring, preloading can occur during the assembly of the delivery device such that a distal biasing force is exerted on the shuttle assembly 14 prior to activation or triggering of the delivery device.

Figure 8:
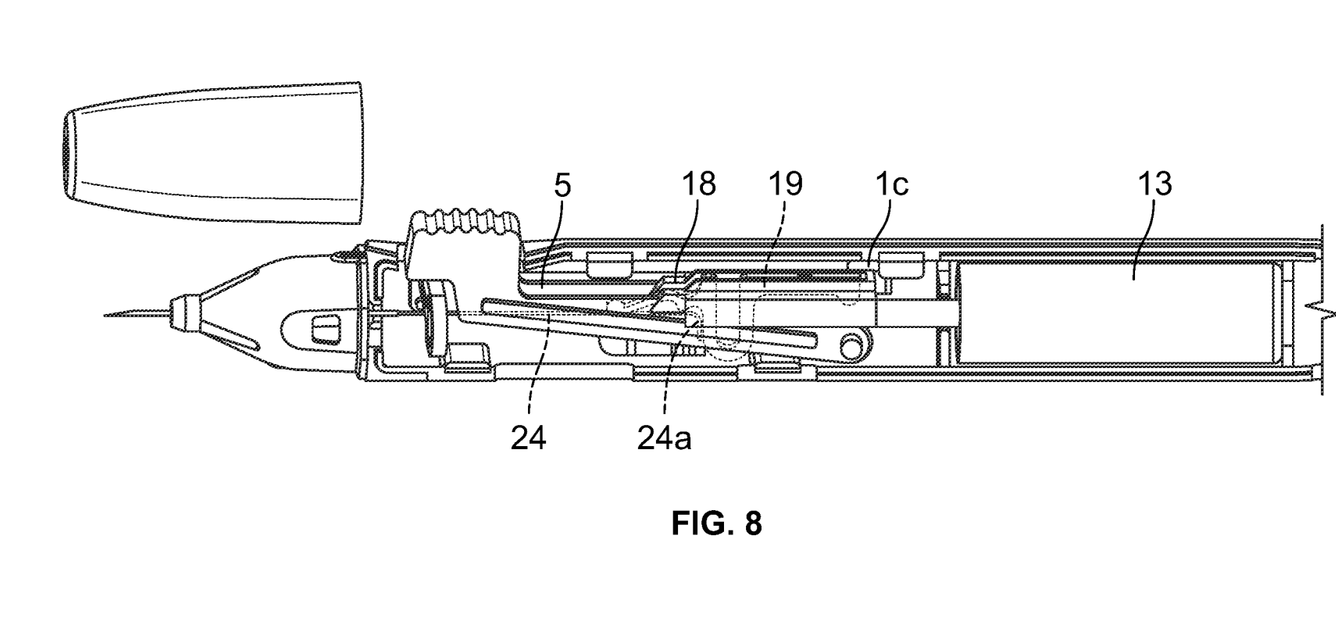
FIG. 8 is a partial cross-sectional view of the delivery device of FIG. 1 illustrating the engagement of the pusher wire with the clamp and the shuttle.

FIG. 2 shows an example of one design of shuttle assembly 14 in operative engagement with housing 1, activation member 5 and dampener assembly 13. The shuttle assembly can generally have a pre-activated state and an activated or fired state. One possible configuration of the shuttle assembly 14 includes a shuttle 18 (see FIG. 3), an elongated shaft 30 connected to a proximal end of the shuttle 18, a friction slider 16, a clamp 19, and a pusher wire 24. The shuttle 18 is rotationally fixed relative to the housing and has a distal end comprising a slot 18a that is configured to accept a portion of the pusher wire 24 such that the pusher wire is axially fixed to the shuttle 18. Slot 18a is also configured to accept clamp 19 once the pusher wire has been inserted into the slot 18a. As indicated in FIG. 8, clamp 19 can be engaged with shuttle 18 and the pusher wire 24 through a pressed fit or snap fit engagement. This press fit engagement prevents axial and rotational movement of the proximal end of pusher wire 24 relative to shuttle 18. Pusher wire 24 is positioned within the slot 18a such that a distal portion of the pusher wire extends axially outward in the distal direction in alignment with longitudinal axis 105. The engagement of pusher wire 24 with shuttle 18 allows the distal end of the pusher wire to move distally and axially simultaneously with the shuttle 18 after activation of the delivery device. During assembly of the delivery device the distal end of the pusher wire is inserted in a sliding relationship in the open proximal end 10b of the needle cannula 10. The distal end of the pusher wire can be shaped to assist in the insertion and sliding engagement within the proximal end of the needle cannula. The proximal end of the pusher wire can be formed, bent or otherwise shaped, such as the hook-shape or L-shape 24a, to aid in the fixation of the pusher wire with an internal surface of slot 18a in shuttle 18.

The shuttle 18 is slidably positioned within the housing 1 and can have a first position, a second position and a third position, where movement from the first position to the second position is in a proximal direction along axis 105. Movement from the second position to the third position is in the distal direction such that when shuttle is in the third position it is positioned and located at a point that is distal relative to the first position. Shuttle 18 also can have sliding surfaces 18b that are operatively engaged with pockets 1e to allow the shuttle assembly 14 to move axially relative to housing 1. A distal end portion of shuttle 18 can have a first latch surface 23 that engages and cooperates with a corresponding second latch surface 22 located on the activation member 5 (see FIG. 5). Engagement of the first and second latch surfaces 22, 23 cooperate to form a sliding latch or trigger. These two latch surfaces are configured to slide relative to each other until a break point is reached where triggering of the delivery device occurs. Relative movement of the two latch surfaces at the break point can generate a tactile or audible notification to the user that implant delivery process has begun. The relative inclination of the latch surfaces can be varied prior to manufacturing to establish an activation force that will result in the break point being reached. One example of this relative inclination is illustrated in FIG. 5 where contact of the first latch surface 23 with the second latch surface 22 defines a plane 102 that is at an angle 103 less than 90 degrees when measured from the proximal facing side of the plane 102 and relative to the longitudinal axis 105.

One benefit of the relative inclination of the latch surfaces occurs at the beginning of the activation process when the activation member 5 is pressed by the user. As the activation member is pushed downward into the housing, the radial movement of the second latch surface 22 relative to the stationary first latch surface 23 causes movement of the shuttle assembly 14 in the proximal direction from the first position to the second position mentioned above. Although the axial movement of shuttle assembly is relatively small, it is sufficient to minimize or eliminate a break force that may have formed between the fiction slider 16 and the inside surface 20 of the dampener housing 15. Minimizing or eliminating the break force allows for a smooth and uninterrupted axial movement of the shuttle assembly 14 in the distal direction, which also results in, and is experienced by the user, a smooth and automatic implant insertion process once the needle cannula is located in the target implant tissue site. Another benefit of the engagement between the activation member and the shuttle is that user can sense or feel a resistance when the activation member is pressed inward into the housing. The frictional relationship between the relative latch surfaces can be predetermined to provide a desired "feel" to the initiation or triggering (activation) of the delivery device. In some cases, it may be desirable to have a frangible relationship between the shuttle and the activation member whereby triggering the activation member will result in the breaking of one or more pieces of a component of the delivery device in order to activate the implant delivery process.

The shuttle assembly 14 can also have an elongated shaft 30 that is axially and rotationally fixed to the shuttle 18 and which extends proximally from the proximal end of shuttle 18. This shaft 30 can have a proximal portion that can comprise keeper 32, 33 and support 31, which as mentioned earlier can be configured not only as a bearing surface for the resilient member, but also to prevent distortion of resilient member 17 during the sliding movement of the shuttle assembly 14 after activation. Keeper 32,33 can be configured as a pair of opposing radial plates that are designed to hold friction slider 16, which as illustrated in FIG. 3 can take the form of an O-ring. The design and materials of fabrication of the friction slider 16 is selected to achieve a desired frictional engagement with the inside surface 20 of the dampener housing 15, and contributing to achieving or setting the distal movement speed of the shuttle assembly and consequently the implant insertion speed once the delivery device has been activated.

One possible method of assembly of the implant delivery device 100 will now be described. Before final assembly of the delivery device, separately, the needle assembly 200 is fabricated as follows:

Needle cannula 10 is fixed to needle holder 25 such that a predetermined bevel 11 orientation is achieved relative to the alignment peg 25a on the needle holder.

Needle cannula and needle holder are secured to the inner needle hub 43 such that the alignment peg 25a cooperates with a corresponding slot 43a in the inner needle hub 43.

The inner needle hub 43 is joined with the outer needle hub 12 by aligning the orientation projections 44, 45 of the inner needle hub with cooperating and keyed slots 12a in the outer needle hub so that the desired bevel orientation is maintained.

Releasably connecting the protective cap 2 onto the outer needle hub 12 such that the distal end of the needle cannula is fully covered and protected from damage.

The shuttle assembly 14, also separately assembled prior to the final assembly of the delivery device, can be assembled as follows:

The friction slider 16 is secured to the proximal end portion of shaft 30;

The proximal end of the pusher wire 24 is placed with the slot 18*a* of the shuttle 18 and securely held in place by inserting the clamp 19 into the slot to form a pressed fit.

The dampener assembly 13 is fabricated by inserting the resilient member 17 into the dampener housing 15, which may have been lubricated before insertion of the resilient member. The proximal end of the shaft 30 of the shuttle assembly 14 is inserted into the open end of the dampener housing and the dampener assembly and shuttle assembly are then positioned in one half section of housing 1. The activation member 5 is then placed in the half housing section. The shuttle assembly is then slid proximally such that the resilient member is loaded or pre-compressed to achieve a distally directed biasing force on the shuttle assembly. The shuttle assembly is moved proximally until the activation member engages with the distal end of the shuttle and the activation member achieves a cocked position or pre-activated state that prevents the shuttle assembly from moving distally. The other half section of the housing is then attached and permanently secured to the first half section of the housing. The lock 3 can then be inserted into the housing through cut-out 1*i* to provide a hard stop that prevents movement of the activation member and premature activation of the delivery device.

The needle assembly is then positioned in a loading apparatus where one or more implants are pushed in through the open proximal end of the needle cannula. The exposed distal end of the pusher wire extending outward from the housing is then guided into the open proximal end of the needle cannula until the outer hub engages and connects with the distal end of the housing forming a permanent attachment.

One method of using the implant delivery device 100 will now be described. First, the user can either remove lock 3 from the housing 1 or remove the protective cap 2 from the outer needle hub 12 to expose the distal end 10*a* of the needle cannula 10. Once the lock and protective cap have been removed, the user then moves the needle cannula to the target implant insertion site and continues moving the needle cannula distally until tissue penetration is achieved by at least the bevel portion of the needle. The user then presses the activation member 5 downward into the housing until the breakpoint between the between the activation member and the shuttle 18 is reached. Reaching and passing the breakpoint causes triggering of the delivery device and movement of the shuttle assembly 14 forward/distally and automatically relative to the housing without further input from the user. The automatic movement of the shuttle assembly likewise causes distal axial movement of the pusher wire 24 which slides distally further inside the needle cannula contacting the one or more implants and pushing the implants within the needle cannula until the implants exit the distal end of the needle cannula and become lodged within the penetrated tissue. Automatic movement of the shuttle assembly, and hence automatic delivery of the implants, is caused by a release of the preloaded biasing force exerted by the resilient member 17 on the shuttle assembly. A steady uninterrupted speed of delivery is also the result of the interaction of the friction slider 16 with the inside of the dampener housing 15 coupled with the steady and deliberate equalization of pressure within the dampener housing that results from the use of vent 40. Simultaneous with the completion of the implant insertion is a visual change in window 4 that is observed by the user. This visual change can occur through a shutter mechanism or shutter effect, for example, where the shuttle 18 moves across the window opening 4 so that user can visually perceive that the window has changed from "filled" to "empty". In addition to a visual notification, the delivery device may provide an audible or tactile indication upon completion of the implant delivery.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments (e.g., of designing and/or utilizing disclosed needles) may be implemented using a variety of materials and methods. Further, it should be appreciated that the present needles and methods of making and operating needles may be used in conjunction with a computer, which may be embodied in any of a number of forms.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedia components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of," or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. All transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An implant delivery device comprising:
an outer housing having a longitudinal axis;
a dampener assembly that controls implantation speed, where the dampener assembly comprises a dampener housing axially fixed relative to the outer housing, where the dampener housing comprises a vent having a predetermined configuration;
a shuttle assembly having an activated state and a fired state, where the shuttle assembly comprises a shuttle slidably positioned within the outer housing and having a first position, a second position and a third position;
a pusher wire axially and rotationally fixed to the shuttle at a proximal end such that a distal end of the pusher wire protrudes away from the shuttle along the longitudinal axis in a distal direction; and
a needle assembly,
wherein the predetermined configuration of the vent directly controls the implantation speed;
wherein the shuttle comprises a first latch surface defining a first angle that is less than 90 degrees when measured relative to the longitudinal axis, wherein the first latch surface is slidably engaged with a second latch surface on an activation member; and
wherein a downward pivoting movement of the activation member causes the sliding movement of the shuttle from the first position to the second position in a proximal direction, and once the second latch surface disengages from the first latch surface, the shuttle moves from the second position to the third position in a distal direction such that the third position is located distally of the first position.

2. The delivery device of claim 1, wherein the vent is a through hole opening that has a predetermined size selected to achieve a predetermined axial speed of the shuttle after activation of the implant delivery device.

3. The delivery device of claim 1, wherein the dampener housing further comprises a proximal end wall and an open distal end, where the vent is positioned within the end wall.

4. The delivery device of claim 1, wherein an inside surface of the dampener housing contains a lubricant.

5. The delivery device of claim 1, wherein the dampener assembly further comprises a resilient member having a first biased state and a second biased state, where the first biased state exerts a greater axial force on the end wall than when in the second biased state.

6. The delivery device of claim 5, wherein the resilient member is a compression spring, a torsion spring, a clock spring or a biased lever arm.

7. The delivery device of claim 5, wherein the resilient member has a proximal end and a distal end, where the proximal end abuts the end wall and a distal end abuts a proximal face of a shaft extending from a proximal end of the shuttle.

8. The delivery device of claim 1, wherein the pusher wire comprises a proximal end that is shaped to extend transversely to the longitudinal axis such that the shaped proximal end is placed within a slot in the shuttle after the distal end of the pusher wire is positioned inside a distal end of the needle assembly, and wherein a clamp is press fit into the slot abutting a portion of the pusher wire such that axial movement of the shuttle causes axial movement of the pusher wire.

9. The delivery device of claim 1, wherein the shuttle further comprises an elongated side surface that is slidably engaged with a pocket located on an inside surface of the outer housing.

10. The delivery device of claim 1, wherein the shuttle assembly further comprises an elongated shaft extending proximally from the shuttle, where the shaft is axially and rotationally fixed to the shuttle.

11. The delivery device of claim 10, wherein a proximal end of the shaft comprises a radially extending plate that supports a friction surface that is slidably engaged with an inner surface of the dampener housing.

12. The delivery device of claim 10, wherein a friction slider is located at a proximal end of the elongated shaft.

13. The delivery device of claim 12, the friction slider comprises two radially extending plates where a friction surface is positioned between the plates.

14. The delivery device of claim 13, where the friction surface is an O-ring.

15. The delivery device of claim 1, wherein the pusher wire is fixed within a slot in the shuttle such that the pusher wire is axially displaceable when the shuttle moves axially relative to the outer housing and a distal end of the needle assembly.

16. The delivery device of claim 8, wherein the proximal end of the pusher wire comprises a hook or L-shape and is engaged with an internal surface of the slot.

17. The delivery device of claim 8 wherein the clamp abuts the proximal end of the pusher wire such that the clamp is axially and rotationally fixed relative to the shuttle.

18. The delivery device of claim 1 further comprising a lock that prevents movement of the activation member.

19. The delivery device of claim 1, wherein the activation member comprises a push surface that protrudes through a cut-out in the outer housing such that push surface is accessible to a user of the delivery device.

20. An implant delivery device comprising:
an outer housing having a longitudinal axis and two pockets positioned longitudinally along an inside surface of the outer housing;
a dampener assembly that controls implantation speed, where the dampener assembly comprises a dampener housing axially fixed relative to the outer housing, where the dampener housing comprises a vent having a predetermined configuration;
a shuttle assembly comprising:
a shuttle having side sliding surfaces operatively engaged with the pockets to prevent rotation of the shuttle relative to outer housing while allowing the shuttle to move proximally from a first position to a second position and then to move distally to a third position, where the third position is distal of the first position; and
an elongated shaft extending from a proximal end of shuttle such that a friction slider on a proximal end of the elongated shaft is slidably positioned inside dampener housing;
a pusher wire axially and rotational fixed to the shuttle at a proximal end such that the pusher wire protrudes away from the shuttle along the longitudinal axis in a distal direction; and
a needle assembly,
wherein the predetermined configuration of the vent directly controls the implantation speed.

\* \* \* \* \*